(12) United States Patent
Locklin

(10) Patent No.: US 9,346,752 B2
(45) Date of Patent: May 24, 2016

(54) PERMANENT ATTACHMENT OF PIGMENTS AND DYES TO SURFACES CONTAINING $C_{alkyl}$-OH FUNCTIONALITY

(75) Inventor: Jason J. Locklin, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 35 days.

(21) Appl. No.: 14/124,035

(22) PCT Filed: Jul. 12, 2012

(86) PCT No.: PCT/US2012/046402
§ 371 (c)(1),
(2), (4) Date: Dec. 5, 2013

(87) PCT Pub. No.: WO2013/012665
PCT Pub. Date: Jan. 24, 2013

(65) Prior Publication Data
US 2014/0134906 A1 May 15, 2014

Related U.S. Application Data

(60) Provisional application No. 61/508,263, filed on Jul. 15, 2011, provisional application No. 61/539,558, filed on Sep. 27, 2011.

(51) Int. Cl.
| | | |
|---|---|---|
| C07C 317/18 | (2006.01) |
| C07C 317/24 | (2006.01) |
| A61K 8/46 | (2006.01) |
| A61K 8/49 | (2006.01) |
| A61Q 5/10 | (2006.01) |
| A61K 8/73 | (2006.01) |
| C07C 279/18 | (2006.01) |
| C07C 305/06 | (2006.01) |
| C07C 305/18 | (2006.01) |
| D06P 1/62 | (2006.01) |

(52) U.S. Cl.
CPC ............... *C07C 317/18* (2013.01); *A61K 8/463* (2013.01); *A61K 8/49* (2013.01); *A61K 8/731* (2013.01); *A61Q 5/10* (2013.01); *C07C 279/18* (2013.01); *C07C 305/06* (2013.01); *C07C 305/18* (2013.01); *C07C 317/24* (2013.01); *D06P 1/627* (2013.01); *A61K 2800/57* (2013.01); *A61K 2800/94* (2013.01); *Y10T 442/20* (2015.04)

(58) Field of Classification Search
None
See application file for complete search history.

(56) References Cited

U.S. PATENT DOCUMENTS

| | | |
|---|---|---|
| 5,811,529 A | 9/1998 | Vines et al. |
| 7,919,221 B2 * | 4/2011 | Asami et al. ................. 430/114 |
| 2004/0250358 A1 | 12/2004 | Gisler et al. |
| 2006/0185556 A1 | 8/2006 | Cho et al. |
| 2008/0216256 A1 | 9/2008 | Freeman et al. |

OTHER PUBLICATIONS

Database Caplus Chemical Abstracts Service, Columbus, Ohio, US; Database Accession No. 2008:63420, Abstract of JP 2008009376, Asami et al., Ricoh Co., Ltd., Japan, Nov. 7, 2008.*
The International Search Report and Written Opinion dated Jan. 3, 2013.

* cited by examiner

*Primary Examiner* — Karl J Puttlitz
(74) *Attorney, Agent, or Firm* — Thomas|Horstemeyer, LLP

(57) ABSTRACT

Embodiment of the present disclosure can include a compound, a structure bonded to the compound, and the like. In an embodiment, the compound can be a linker between an agent and a structure, where the agent can be a dye or a pigment and the structure can be a fiber, hair, or another structure.

2 Claims, 1 Drawing Sheet

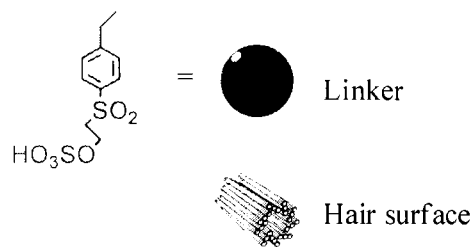
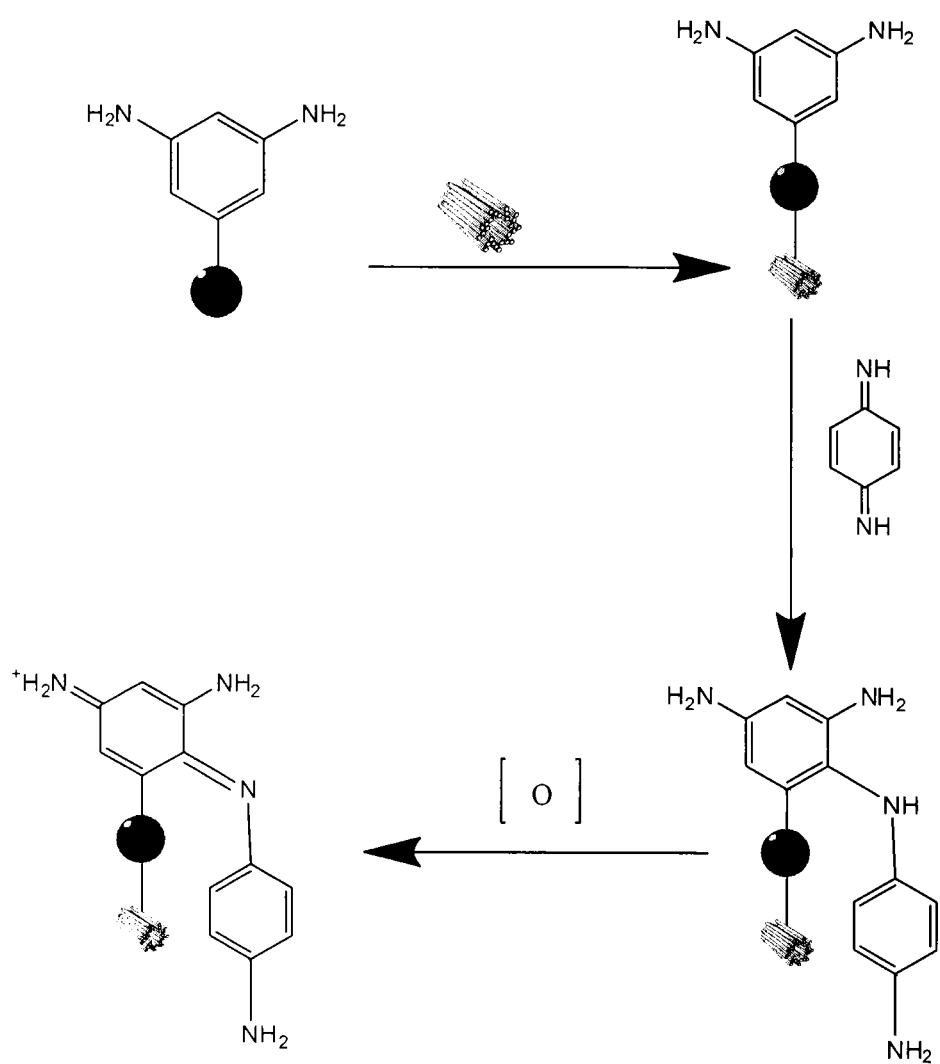

PERMANENT ATTACHMENT OF PIGMENTS AND DYES TO SURFACES CONTAINING $C_{alkyl}$-OH FUNCTIONALITY

CROSS REFERENCE TO RELATED APPLICATION

This application is the 35 U.S.C. §371 national stage of PCT application having serial number PCT/US2012/046402, filed on Jul. 12, 2012. This application also claims priority to U.S. provisional application entitled "PERMANENT ATTACHMENT OF PIGMENTS AND DYES TO SURFACES CONTAINING $C_{ALKYL}$-OH FUNCTIONALITY," having Ser. No. 61/508,263, filed on Jul. 15, 2011, which is entirely incorporated herein by reference. In addition, this application claims priority to U.S. provisional application entitled "PERMANENT ATTACHMENT OF PIGMENTS AND DYES TO SURFACES CONTAINING $C_{ALKYL}$-OH FUNCTIONALITY," having Ser. No. 61/539,558, filed on Sep. 27, 2011, which is entirely incorporated herein by reference.

BACKGROUND

Covalent attachment of dyes and pigments to structures such as fabrics and hair can be challenging. Thus, solutions to attaching dyes and pigments to structures is actively being pursued.

SUMMARY

Embodiment of the present disclosure can include a compound, a structure bonded to the compound, and the like. In an embodiment, the compound can be a linker between an agent and a structure, where the agent can be a dye or a pigment and the structure can be a fiber, hair, or another structure.

An embodiment of the compound, among others, can be represented by the following formula:

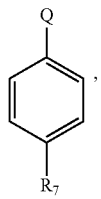

wherein Q is selected from the group consisting of: a linear, branched, or cyclic, a substituted or unsubstituted, aliphatic group, a substituted or unsubstituted aryl group, a substituted or unsubstituted heteroaryl group, an oxygen containing group, an amine group, a sulfur group, and a combination thereof; and R7 are selected from:

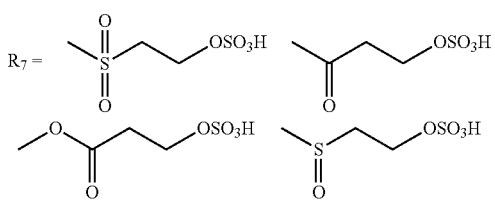

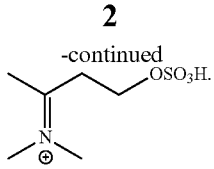

An embodiment of the structure, among others, includes: a compound having the following formula:

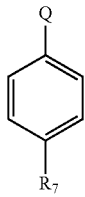

wherein Q is selected from the group consisting of: a linear, branched, or cyclic, a substituted or unsubstituted, aliphatic group, a substituted or unsubstituted aryl group, a substituted or unsubstituted heteroaryl group, an oxygen containing group, an amine group, a sulfur group, and a combination thereof; and R7 are selected from:

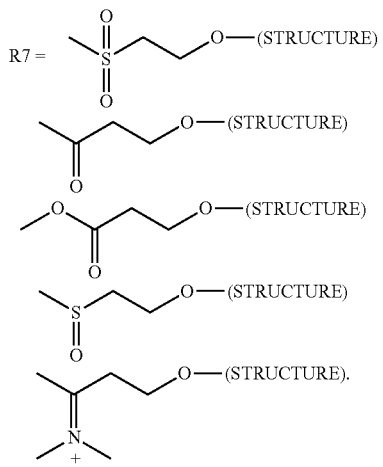

wherein the structure includes $C_{alkyl}$-OH functionality.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views FIG. 1 illustrates an embodiment of the present disclosure.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, polymer chemistry, biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

The term "substituted" refers to any one or more hydrogens on the designated atom that can be replaced with a selection from the indicated group, provided that the designated atom's normal valence is not exceeded, and that the substitution results in a stable compound.

The term "aliphatic group" refers to a saturated or unsaturated linear or branched hydrocarbon group and encompasses alkyl, alkenyl, and alkynyl groups, for example.

As used herein, "alkyl" or "alkyl group" refers to a saturated aliphatic hydrocarbon chain and a substituted saturated aliphatic hydrocarbon chain which may be straight, branched, or cyclic, having 1 to 20 carbon atoms, where the stated range of carbon atoms includes each intervening integer individually, as well as sub-ranges. Examples of alkyl groups include, but are not limited to, methyl, ethyl, i-propyl, n-propyl, n-butyl, t-butyl, pentyl, hexyl, septyl, octyl, nonyl, decyl, and the like. The substitution can be with a halogen, for example.

As used herein, "alkenyl" or "alkenyl group" refers to an aliphatic hydrocarbon which can be straight or branched, containing at least one carbon-carbon double bond, having 2 to 20 carbon atoms, wherein the stated range of carbon atoms includes each intervening integer individually, as well as sub-ranges. Examples of alkenyl groups include, but are not limited to, ethenyl, propenyl, n-butenyl, i-butenyl, 3-methylbut-2-enyl, n-pentenyl, heptenyl, octenyl, decenyl, and the like.

The term "alkynyl" refers to straight or branched chain hydrocarbon groups, containing at least one triple carbon to carbon bond having 2 to 20 carbon atoms, wherein the stated range of carbon atoms includes each intervening integer individually, as well as sub-ranges. An alkynyl group can be optionally substituted, unless stated otherwise, with one or more groups.

The term "arylalkyl" refers to an arylalkyl group wherein the aryl and alkyl are as herein described. Examples of arylalkyl include, but are not limited to, -phenylmethyl, -phenylethyl, -phenylpropyl, -phenylbutyl, and -phenylpentyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Examples are furanyl, pyranyl, thienyl, imidazyl, pyrrolyl, pyridyl, pyrazolyl, pyrazinyl, pyrimidinyl, indolyl, quinolyl, isoquinolyl, quinoxalyl, and quinazolinyl. Preferred examples are furanyl, imidazyl, pyranyl, pyrrolyl, and pyridyl.

The term "substituted," as in "substituted alkyl", "substituted cycloalkyl," "substituted cycloalkenyl," substituted aryl," substituted biaryl," "substituted fused aryl", and the like, for example, means that the substituted group may contain in place of one or more hydrogens a group such as hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl group in which one or more hydrogens are substituted by halogen radicals. Examples of haloalkyl include, but are not limited to, trifluoromethyl, trichloromethyl, pentafluoroethyl, and pentachloroethyl.

As used herein, the term "fiber" refers to filamentous material that can be used in fabric and yarn as well as textile fabrication. One or more fibers can be used to produce a fabric or yarn. Fibers include, without limitation, materials such as cellulose, fibers of animal origin (e.g., alpaca, angora, wool and vicuna), hemicellulose, lignin, polyesters, polyamides, rayon, modacrylic, aramids, polyacetates, polyxanthates, acrylics and acrylonitriles, polyvinyls and functionalized derivatives, polyvinylidenes, PTFE, latex, polystyrene-butadiene, polyethylene, polyacetylene, polycarbonates, polyethers and derivatives, polyurethane-polyurea copolymers, polybenzimidazoles, silk, lyocell, carbon fibers, polyphenylene sulfides, polypropylene, polylactides, polyglycolids, cellophane, polycaprolactone, "M5" (poly{diimidazo pyridinylene (dihydroxy)phenylene}), melamine-formadehyde, plastarch, PPOs (e.g., Zylon®), polyolefins, and polyurethane.

The term "textile article" can include garments, fabrics, carpets, apparel, furniture coverings, drapes, upholstery, bedding, automotive seat covers, fishing nets, rope, articles including fibers (e.g., natural fibers, synthetic fibers, and combinations thereof), articles including yarn (e.g., natural fibers, synthetic fibers, and combinations thereof), and the like.

DISCUSSION

An embodiment of the present disclosure includes a compound, a structure bonded to the compound, and the like. In an embodiment, the compound can be a linker between an agent and a structure, where the agent can be a dye or a pigment and the structure can be a fiber, hair, or another structure.

In an embodiment, the compound can be used to bind to a structure that includes $C_{alkyl}$-OH functionality. In an embodiment, the structure inherently has a $C_{alkyl}$-OH functionality on the surface or assessable to bond to the compound. In an embodiment, the surface or structure can be coated with a film or a material (functionalized layer) that has a $C_{alkyl}$-OH functionality. In an embodiment, the structure can include a cellulose-based material, a polypropylene fiber, a polyethylene fiber, a polyester fiber, a polyamide fiber, an aramid fiber, and a natural fiber or natural surfaces, or other surfaces or structures having (e.g., inherently or coated with a film) $C_{alkyl}$-OH functionality.

In addition, the compound can be bonded to a pigment or dye. In this regard, a compound, including the pigment or dye, can be attached to a surface or structure having $C_{alkyl}$-OH functionality. In addition, the compound can be used to bind to a surface or structure having $C_{alkyl}$-OH functionality such as hair, textile article, counters, processing equipment, utensils, food packaging materials, metals, plastic structures, medical instruments, medical implants, diapers, leathers, flooring, and the like, so that a dye or pigment can be attached to these surfaces or structures.

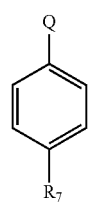

In an embodiment, the compound can be represented as indicated above. In an embodiment, Q can be an aliphatic group (substituted or unsubstituted and/or linear, branched, or cyclic) (e.g., alkyl, alkenyl, alkynyl), an aryl group (substituted or unsubstituted), a heteroaryl group (substituted or unsubstituted), an oxygen group (e.g., O—R1'), an amine group (e.g., primary, secondary, or tertiary, where each can have an appropriate number of R1' groups that are independently selected), a sulfur group (e.g., S—R1' (one ore more R1' can be included)), and the like. In an embodiment, R1' can be an aliphatic group (substituted or unsubstituted and/or linear, branched or cyclic), an aromatic group (substituted or unsubstituted), an aryl group (substituted or unsubstituted), a heteroaryl group (substituted or unsubstituted), and the like.

In an embodiment, $R_7$ can be selected from the following groups:

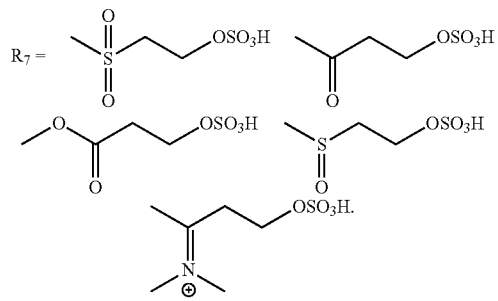

In an embodiment, the groups noted above can be substituted or unsubstituted.

In an embodiment, the compound can be attached to the pigment or dye via Q, while the compound is attached to the structure having $C_{alkyl}$-OH functionality via $R_7$ (where $SO_3H$ has been removed during the reaction). For example, R7, when it is attached to a structure, can be represented as shown below:

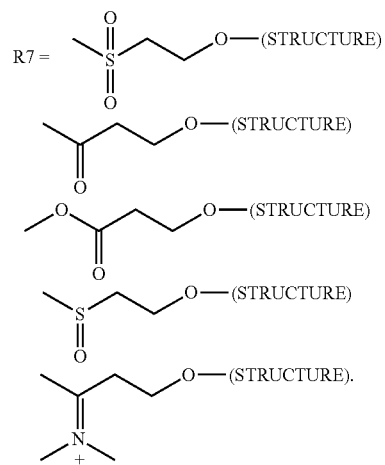

As noted above, the compound can be attached to pigments and dyes. Although not intending to be limited to the dyes and pigments described herein, the following presents some illustrative examples of dyes and pigments.

Organic pigments are varied in their structures and functionalities. However, the most common pigments are derivatives of aromatic amines, quinones, azo compounds, or quinonediimines. The structures of some common pigments/dyes appear below, without any intent to limit the applicability of this technology to the pigments described herein:

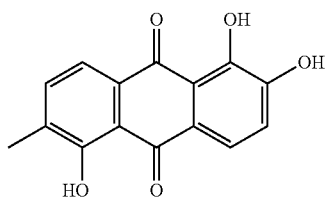 [SMILES: Cc1ccc2c(c1O)C(=O)c1ccc(O)c(O)c1C2=O]

Morindone [CAS 478-29-5], a red compound that requires a mordant and may yield different shades of red depending on the mordant used.

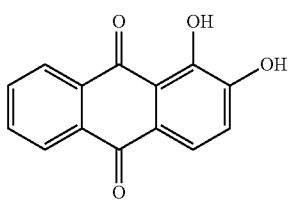 [SMILES: O=C1c2ccccc2C(=O)c2c1ccc(O)c2O]

Alizarin [CAS 72-48-0], also a red dye, frequently used in the textile industry.

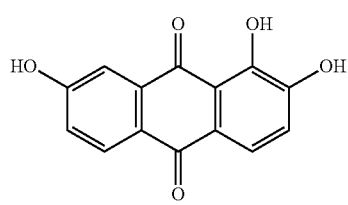 [SMILES: O=C1c2ccc(O)cc2C(=O)c2c1ccc(O)c2O]

Anthrapurpurin [CAS 602-65-3], a purple dye

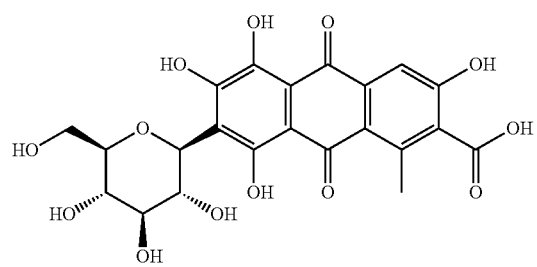 [SMILES: Cc1c(C(=O)O)c(O)cc2c1C(=O)c1c(O)c([C@@H]3O[C@H](CO)[C@@H](O)[C@H](O)[C@H]3O)c(O)c(O)c1C2=O]

Carminic acid [CAS 1260-17-9], a naturally occurring dye with a crimson color

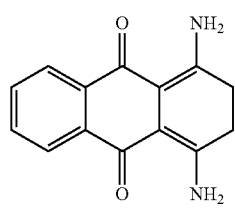 [SMILES: NC1=C2C(=O)c3ccccc3C(=O)C2=C(N)CC1]

1,4-Diamino-2,3,dihudroanthraquinone [CAS 81-63-0], also known as Disperse Red 9 or Solvent Violet 47, an important industrial dye.

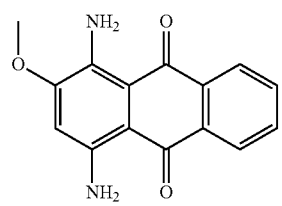 [SMILES: COc1cc(N)c2c(c1N)C(=O)c1ccccc1C2=O]

1,4-diamino-2-methoxy anthraquinone, [CAS 2872-48-2], also known as Disperse Red 11 or C.I. 62015 is a common red dye.

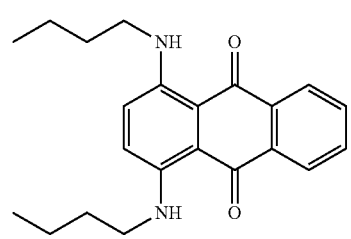 [SMILES: CCCCNc1ccc(NCCCC)c2c1C(=O)c1ccccc1C2=O]

1,4-bis(butylamino) anthraquinone [CAS 17354-14-2], also called Oil Blue 35, Solvent Blue 35, Blue 2N, Blue B, Oil Blue B, 1,4-bis(butylamino) anthraquinone and CI 61554 is a deep blue dye

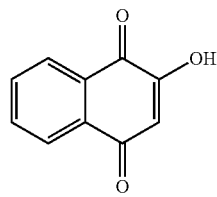 [SMILES: O=C1C=C(O)C(=O)c2ccccc21]

Lawsone (2-hydroxy-1,4-naphthoquinone), also known as hennotannic acid [CAS 83-72-7] is a naturally occurring dye derived from the henna plant, which renders skin and hair surfaces with a tint ranging from orange to brown. It is also used a as natural UV filter in sunless tanning sunscreens.

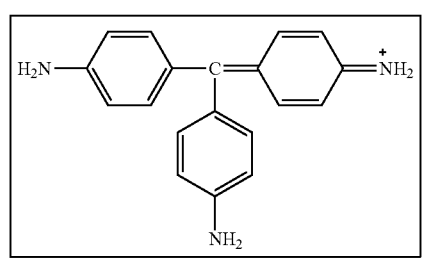 [SMILES: Nc1ccc(C(=C2C=CC(=[NH2+])C=C2)c2ccc(N)cc2)cc1]

Pararosaniline (Basic red 9; C.I. 42500; [CAS 569-61-9] is a magenta/red dye. When modified by successive methylation of the amino groups, it yields several other important pigments, as below Methyl green
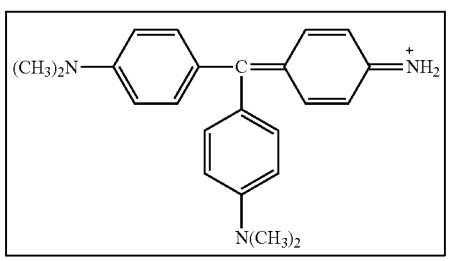
Methyl violet
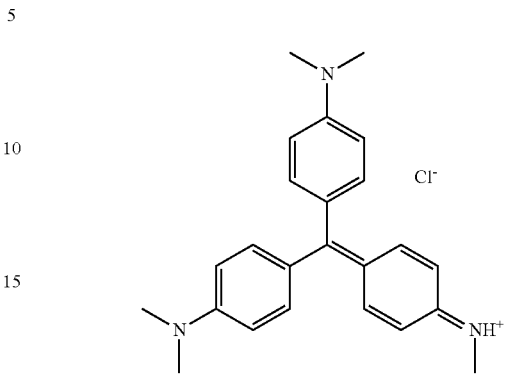
Methyl violet 2B [8004-87-3]
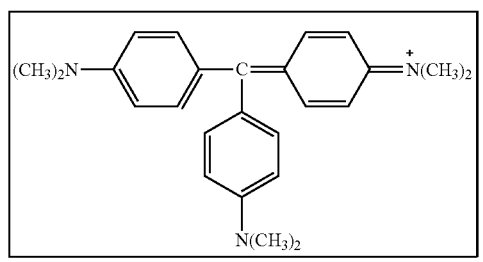
Crystal violet (Methyl violet 10B; [548-62-9]
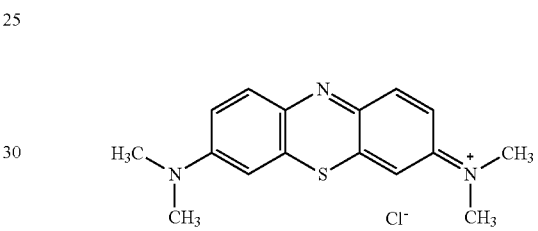
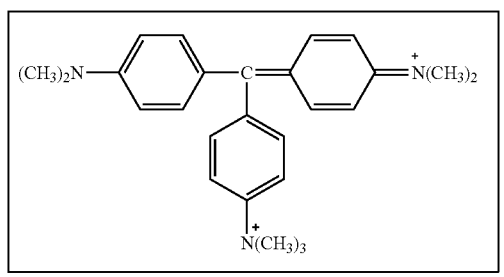
Methylene blue [61-73-4] is an example of a blue pigment used only in temporary staining and normally not used in the textile industry, but that can be permanently attached to surfaces using the chemistry described herein.
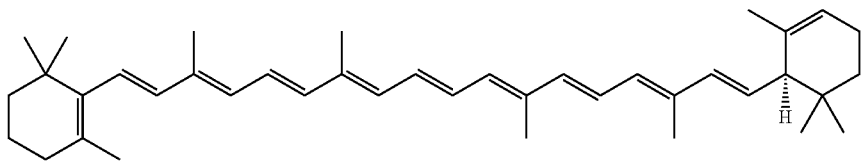
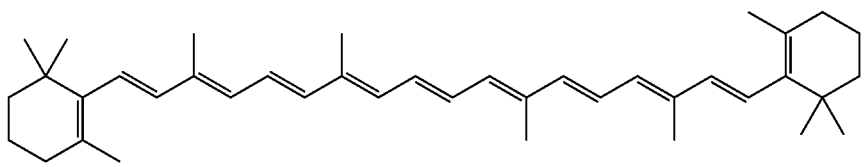
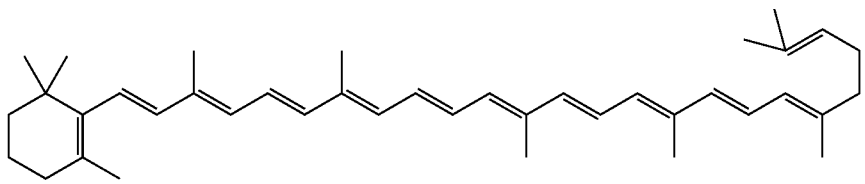

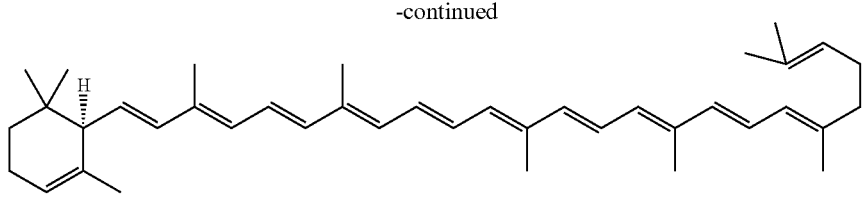

Carotenes, which are yellow-orange pigments

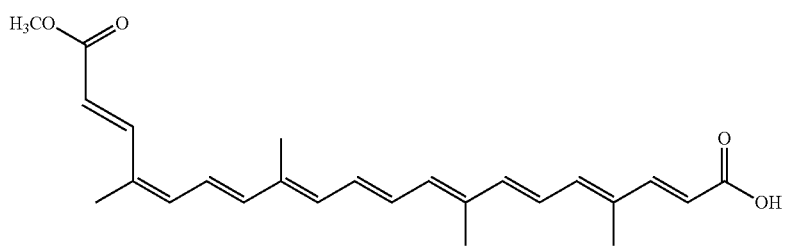 [SMILES: COC(=O)/C=C/C(C)=C\C=C\C(C)=C\C=C\C=C(C)\C=C\C=C(C)\C=C\C(=O)O]

Bixin (annatto) is a natural pigment with an intense orange color, normally used in the food industry, and not in the textile industry. As with other dyes/pigments, it can be permanently affixed onto C—OH containing surfaces through the use of this technology.

Other common dyes include:

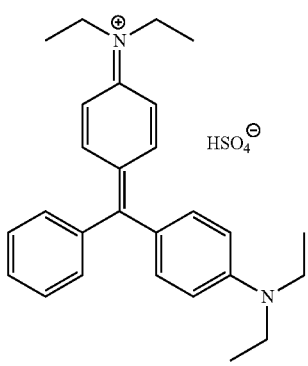

Brilliant Green [633-03-04]

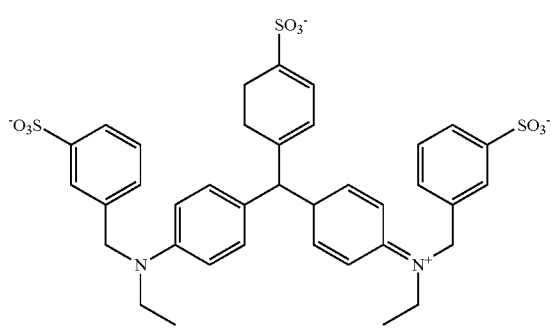

Light Green SF yellowish (FD&C Green #2, Pencil Green CF) [5141-20-8]

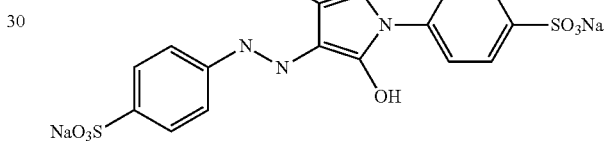

Tartrazine, E102, FD&C Yellow 5 [1934-21-0], which is a lemon-yellow dye

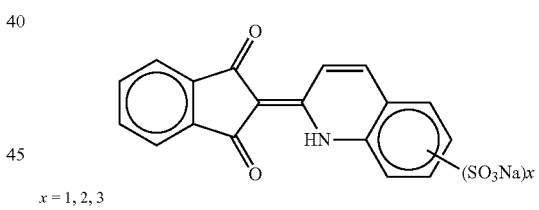

$x = 1, 2, 3$

Quinoline yellow, C.I. 47005, Food Yellow 13 CAS [8004-92-0]

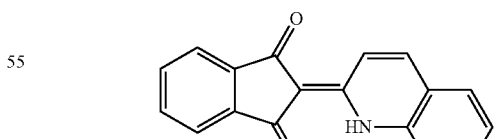

Quinoline yellow SS [8003-22-3]

EXAMPLE

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Permanent Affixation of Pigments and Dyes onto Surfaces

The method used herein benefits from the reactivity of $C_{alkyl}$-OH functionality toward sulfonic acid to yield a sulfonic ester (or organic sulfate) through the covalent attachment of the $SO_4$ unit to the alkyl group.

A ligating agent for which the structure (A) is shown below, can be used to form a derivative of a dye (e.g., (B) and (C) below) which is then permanently attached to a substrate by simple esterification reaction (e.g., (D), using cellulose as the substrate). Other linkers described herein can also be attached in a similar manner.

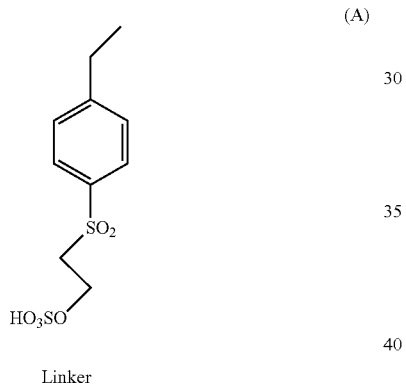

(A)

Linker

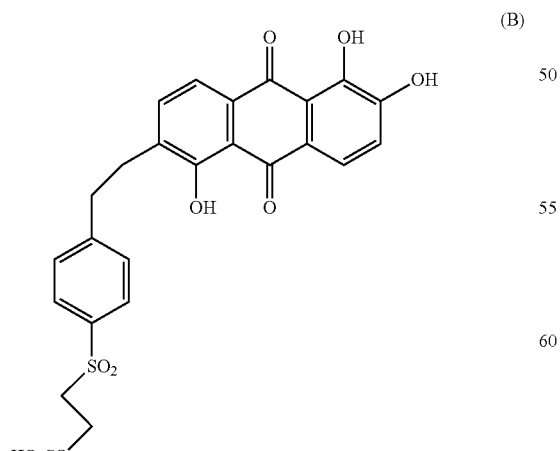

(B)

Morindone derivative

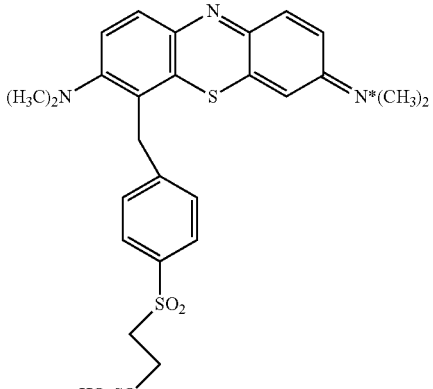

(C)

Methylene Blue Derivative

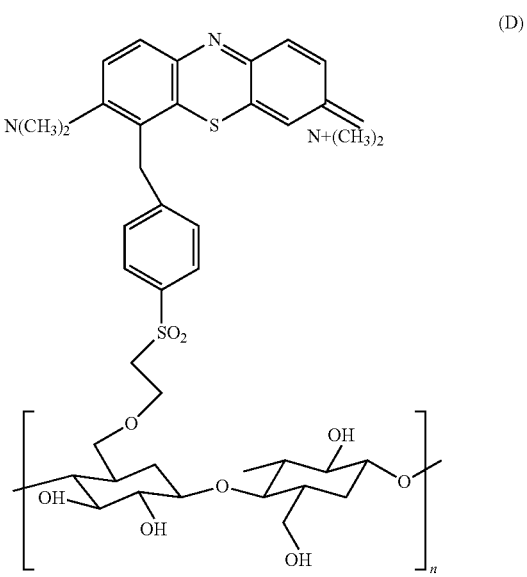

(D)

Methylene blue dye permanently attached to cellulose

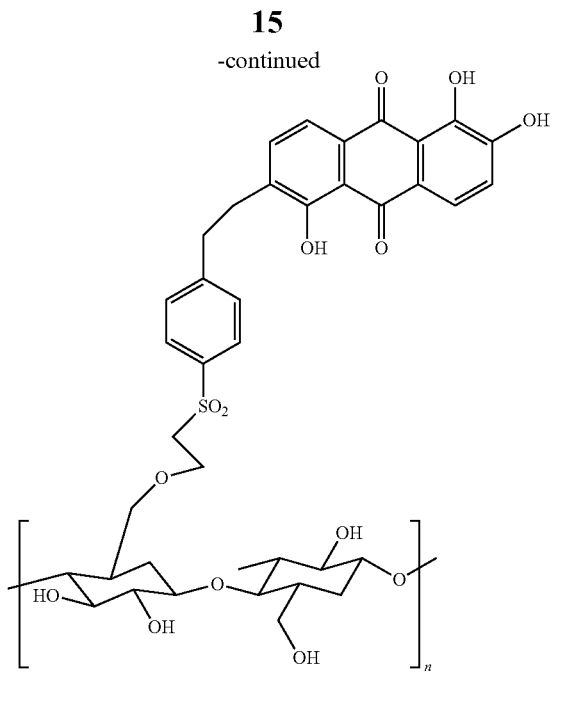

Morindone derivative permanetly attached to cellulose

It will be apparent for someone skilled in the art that the Linker (A) (as well as other linkers described herein) may be attached to any of the pigments described herein and their derivatives, then the complex is reacted with $C_{alkyl}$-OH functionalities to covalently attach pigments to those surfaces or structures.

Example 2

Permanent Attachment of Dyes to Hair

The most popular way to achieve permanent hair coloring is through the use of oxidation dyes. The ingredients include 1,4-diaminobenzene (historically) or 2,5-diaminotoluene (currently), a coupling agent, and an oxidant. The process is typically performed under basic conditions.

The mechanism of oxidation dyes involves three steps: 1) Oxidation of 1,4-diaminobenzene derivative to the quinone state. 2) Reaction of this diimine with a coupler (more detail below). 3) Oxidation of the resulting compound to give the final dye. The preparation (dye precursors) is in the leuco (colorless) form. Oxidizing agents are usually hydrogen peroxide, and the alkaline environment is usually provided by ammonia. The combination of hydrogen peroxide and the primary intermediate causes the natural hair to be lightened, which provides a blank canvas for the dye. Ammonia opens the hair shaft so that the dye can actually bond with the hair, and ammonia speeds up the reaction of the dye with the hair.

Various combinations of primary intermediates and couplers provide a spectrum of shades of hair colors. The primary intermediates are aromatic para compounds, such as 1,4-diaminobenzene or 4-aminophenol. The couplers are meta-substituted derivatives of aniline. They come in three major classes based on the color that they produce when they react with the primary intermediate.

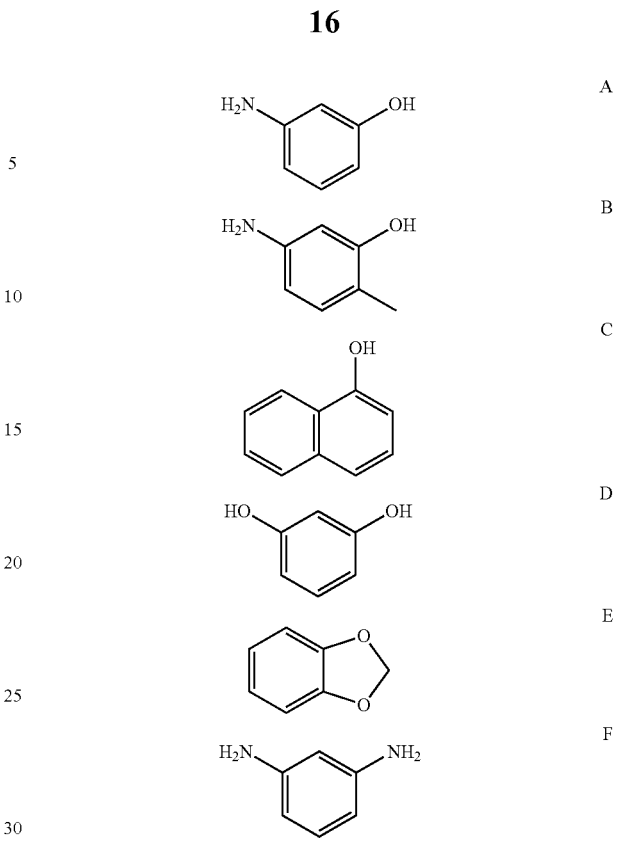

Couplers are chemical compounds that define the color of the hair dye. As shown above are three red couplers (A,B,C), two yellow-green couplers (D,E) and a blue coupler (F).

Blue couplers include 1,3-diaminobenzene and its derivatives.

Red couplers include phenols and naphthols, such as 3-aminophenol (CAS#591-27-5), 5-amino-2-methylphenol (CAS#2835-95-2) and 1-naphthol (CAS#90-15-3). The combination of 2,5-diaminotoluene with the coupler 3-aminophenol gives a magenta-brown dye, while the combination of 2,5-diaminotoluene with the coupler 1-naphthol gives a purple dye.

Yellow-green couplers include resorcinol, 4-chlororesorcinol, and benzodioxoles. These compounds produce broadband absorption when they react to form dyes, allowing for more natural-looking hair colors. The combination of 2,5-diaminotoluene with the coupler resorcinol gives a greenish brown dye.

The first step shows the oxidation of p-phenylenediamine to the quinonediimine $(C_6H_4(NH)_2)$:

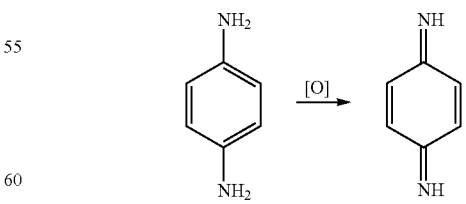

This species exists in equilibrium with the monoprotonated form $(C_6H_4(NH)(NH_2)^+)$ (not shown). The second step involves the attack of this quinonediimine on the coupler. In organic chemistry, this reaction is called electrophilic aromatic substitution:

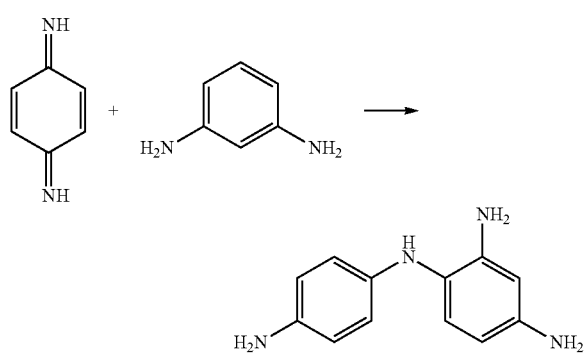

In the third and final step, the product from the quinonediimine-coupler reaction oxidizes to the final hair dye.

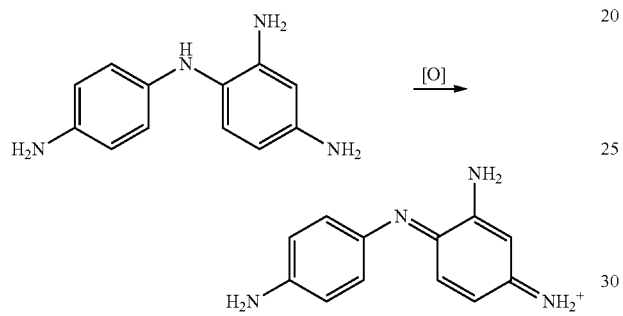

The resulting hair dye is also much larger than the precursor molecules, which causes the dye to bond to the hair.

One embodiment of the present disclosure permits the permanent coloring of hair (especially bleached hair), using a strategy that is similar to that used above. The compound, or linker (A) above, (as well as others described herein) may be used to affix the coupler to hair, following the reaction with quinonediimine and oxidation (See FIG. 1).

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to the values and/or measuring techniques. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A compound comprising a formula:

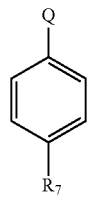

wherein Q is selected from the group consisting of: a linear, branched, or cyclic, a substituted or unsubstituted, aliphatic group, a substituted or unsubstituted aryl group, and R7 is

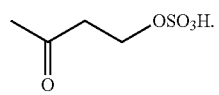

2. The compound of claim 1, wherein Q is a linear, branched, or cyclic, a substituted or unsubstituted, aliphatic group.

* * * * *